United States Patent [19]

Lonn et al.

[11] Patent Number: 4,870,666
[45] Date of Patent: Sep. 26, 1989

[54] COMPUTER TOMOGRAPHIC PHANTOM

[75] Inventors: Albert H. R. Lonn, Wauwatosa, Wis.; Donald R. Jacobson; David J. Zech, both of Waukesha, Wis.

[73] Assignee: General Electric Company, N.Y.

[21] Appl. No.: 894,287

[22] Filed: Aug. 7, 1986

[51] Int. Cl.$^4$ .............................................. H05G 1/60
[52] U.S. Cl. ...................................... 378/18; 378/207
[58] Field of Search .................. 378/15, 208, 56, 54, 378/18, 207; 128/92 R; 450/94

[56] References Cited

U.S. PATENT DOCUMENTS

| | | | |
|---|---|---|---|
| 1,049,692 | 1/1913 | Franklin | 450/94 |
| 4,124,799 | 11/1978 | Schittenhelm | 378/18 |
| 4,181,858 | 1/1980 | Moore | 378/18 |
| 4,233,507 | 11/1980 | Volz | 378/207 |
| 4,651,335 | 3/1987 | Kalender et al. | 378/207 |
| 4,782,502 | 11/1988 | Schuly | 378/18 |

*Primary Examiner*—Craig E. Church
*Attorney, Agent, or Firm*—Thomas R. Morrison

[57] ABSTRACT

A reference phantom system for quantitative computer tomography employs a flexible reference phantom with means for urging the flexible reference phantom into contact along the curved surface of the lumbar region of a human patient. In one embodiment, the reference phantom is pre-curved in an arc greater than required. Pressure from the weight of a patient laying upon the reference phantom is effective for straightening out the curvature sufficiently to achieve substantial contact along the lumbar region. The curvature of the reference phantom may be additionally distorted by a resilient pad between the resilient phantom and a table for urging it into contact with the lumbar region. In a second embodiment of the invention, a flexible reference phantom is disposed in a slot in the top of a resilient cushion. The flexibility of the reference phantom and the stiffness of the resilient cushion are matched so that the reference phantom is deformed as it is urged into contact with the lumber region of a patient whereby substantially continuous contact is achieved with the reference phantom along substantially the entire contiguous length of the lumbar region. The resilient cushion and reference phantom may be enclosed in a flexible container. A partially curved reference phantom is a slot in a resilient cushion is also contemplated.

6 Claims, 2 Drawing Sheets

COMPUTER TOMOGRAPHIC PHANTOM

BACKGROUND OF THE INVENTION

The present invention relates to radiation devices and, more particularly, to devices for use with ionizing radiation capable of providing a calibrated reference image with which elements of a detected image may be compared.

As is well known, computer aided tomography (CAT) techniques employ a source of ionizing radiation positioned at one location with respect to a body, and one or more detectors positioned at the opposite side of the body. The source and detectors are moved together in a scanning arc about the body while the outputs of the detectors are stored as a measure of the attenuation of the body at a plurality of positions about the arc. Typically, the arc encompasses a 360-degree circle about the body and attenuation measurements are made at, for example, one-degree intervals.

The above scanning technique produces a matrix of attenuation values for the various angles conventionally processed by computer to yield reconstructed images having image densities related to the attenuation of tissue in at least one transverse slice through the body.

Some applications of computer tomography require more quantitative results than the imaging applications discussed above. For example, U.S. Pat. No. 4,124,799 discloses an elastic belt containing test bodies strapped about a patient within the field of view of the scanning apparatus. The test bodies contain calibrated concentrations of materials whose presence in the resulting reconstructed image provides a set of known reference values for comparison with the images of nearby tissue to calculate a radiation dosage for later radiation treatment.

The technique of strapping an elastic belt about the patient's body is less than satisfactory for quantitative computer tomography of a human spine. One significant application of such techniques is in determining the chemical content of the spongy bone, also called the trabecular bone, in the human spinal column. Of particular interest is the amount of calcium-containing compounds in the bone. A quantitative measurement of calcium in the spongy bone permits diagnosis and treatment of certain bone-degenerative diseases.

A reference phantom containing graduated concentrations of bone-reference materials for quantitative spinal imaging is disclosed in U.S. Pat. No. 4,233,507, of common assignee with the present application. Other reference phantoms are described in papers "*Comparison of Vertebral and Peripheral Mineral Losses in Disuse Osteoporosis in Monkeys*"; Cann CE, Genant HK, Young DR; RADIOLOGY, 134:525-529, February 1980; (presented as work-in-progress at the Radiological Society of North America meeting in November 1978); and "*Integral Approach to Vertebral Bone Mineral Analysis by X-Ray CT*"; Kalendar WA, Suess C, Kotz E; presented as work-in-progress and Scientific Exhibit at Radiological Society of North America meeting in November 1985.

The above cited reference phantoms include rigid plates either embedded in, or disposed parallel to, the supporting table and containing the reference material. In the above patent and papers, the reference material is incorporated into, or laid atop, a planar or transversely curved table top.

The curvature of the human spinal column produces an air gap between the reference phantom and the patient's back. The air gap induces shading and streak artifacts capable of affecting the reference values, thus leading to possible errors in quantifying the results of the measurements. The above patent proposes reducing the size of the gap by raising the knees of the patient to reduce the angle of the pelvis. Even when this is done, however, a substantial curvature, and resulting air gap, remains.

The above papers propose that improved accuracy of determining bone-mineral values may be achieved by coupling the reference phantom to the patient using, for example, an intermediate material substantially filling the air gap and having a response approximating that of water. One material which appears to be satisfactory for this purpose is a bolus, or flexible container, filled with water and positioned between the reference phantom and the back of the patient. The addition of a bolus of water-equivalent material is undesirable since it attenuates the portion of the X-ray beam passing through it by a factor of as much as 3 and increases the statistical error in the measurements due to increased photon noise. Besides a water-filled flexible bag, other coupling materials such as, for example, gels and powders having properties corresponding to those of water, have been used. Such other coupling materials, having properties equivalent to water, share the undesirable results of water itself. .This paper also proposes that edge effects caused by off-focal radiation may be minimized by encapsulating the sample materials in the reference phantom in a near-water-equivalent material such as, for example, an acrylic.

OBJECTS AND SUMMARY OF THE INVENTION

Accordingly, it is an object of the invention to provide a reference phantom for quantitative computer tomography which overcomes the drawbacks of the prior art.

It is a further object of the invention to provide a reference phantom having means for close coupling to the spinal region of a human being without requiring an intervening coupling material.

It is a still further object of the invention to provide a reference phantom including means for conforming the reference phantom to the spinal region of a human being.

It is a still further object of the invention to provide a reference phantom including reference materials encapsulated in a flexible assembly effective for conforming to the spinal region of a human being.

It is a still further object of the invention to provide a reference phantom assembly in which a flexible reference phantom is packaged with a resilient material. The resilient material has a resilience in relation to the flexibility of the reference phantom effective to conform the reference phantom to the back of a human being under the weight of the human being.

Briefly stated, the present invention provides a reference phantom system for quantitative computer tomography employing a flexible reference phantom with means for urging the flexible reference phantom into contact along the curved surface of the lumbar region of a human patient. In one embodiment, the reference phantom is pre-curved in an arc greater than required. Pressure from the weight of a patient laying upon the reference phantom is effective for straightening out the curvature sufficiently to achieve substantial contact along the lumbar region. The curvature of the reference phantom may be additionally distorted by a resilient pad between the resilient phantom and a table for urging it into contact with the lumbar region. In a second embodiment of the invention, a flexible reference phantom is disposed in a slot in the top of a resilient cushion. The flexibility of the reference phantom and the stiffness of the resilient cushion are matched so that the reference phantom is deformed as it is urged into contact with the lumbar region of a patient, whereby substantially continuous contact is achieved with the reference phantom along substantially the entire contiguous length of the lumbar region. The resilient cushion and reference phantom may be enclosed in a flexible container. A partially curved reference phantom in a slot in a resilient cushion is also contemplated.

According to an embodiment of the invention, there is provided a reference phantom for quantitative computer tomography comprising: a flexible bar containing a plurality of reference materials, and means for deforming a curvature of the flexible bar into substantially continuous contact with a contiguous region of a body of a patient.

According to a feature of the invention, there is provided a reference phantom for quantitative computer tomography comprising: a flexible bar containing a plurality of reference materials, a resilient cushion having a dimension substantially co-extensive with a contiguous region of a patient, a slot in an upper surface of the resilient cushion, the flexible bar being disposed in the slot, a flexibility of the bar and a stiffness of the resilient cushion being effective, in combination, for urging a surface of the reference phantom into contact along substantially all of the contiguous region.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
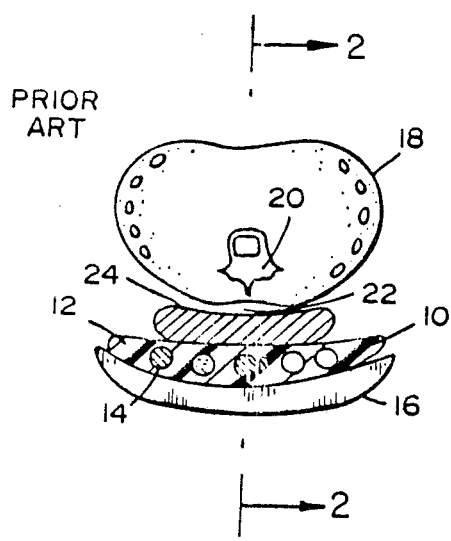
FIG. 1 is a transverse cross section of a patient and a reference phantom according to the prior art.

Referring to FIG. 1, there is shown at 10, a reference phantom according to the prior art. An encapsulating material 12 contains a plurality of reference bodies 14 having X-ray attenuation properties corresponding to those of interest. A table 16 supports reference phantom 10, as well as the weight of a patient 18 resting thereon, with the patient's spinal column 20 centered on reference phantom 10.

Figure 2:
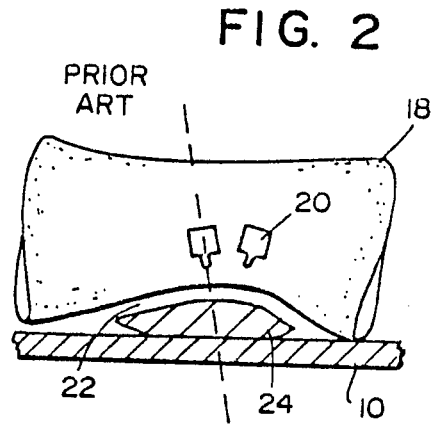
FIG. 2 is a longitudinal cross section taken along II—II in FIG. 1.

Referring now also to FIG. 2, a normal curvature of spinal column 20, particularly in the lumbar region, produces a substantial air gap 22 between reference phantom 10 and patient 18. A flexible bolus 24 of a material-, having an X-ray attenuation characteristic corresponding to that of water at all X-ray energies of interest, is disposed between patient 18 and reference phantom 10, whereby air gap 22 is substantially filled. Flexible bolus 24 may be a rubber or flexible plastic container filled with water, a gel, or a powdered material having equivalent X-ray attenuation characteristics. As previously noted, although it solves some problems, the presence of flexible bolus 24 attenuates the X-rays passing therethrough and degrades the ability to discriminate material concentrations in spinal column 20. For example, X-radiation in the energy range of interest, is attenuated about 50 percent in passing through a one-inch thickness of a water-equivalent material. Spinal curvatures requiring thicknesses of 1.5 to 2 inches of flexible bolus 24 for coupling are encountered routinely.

Figure 3:
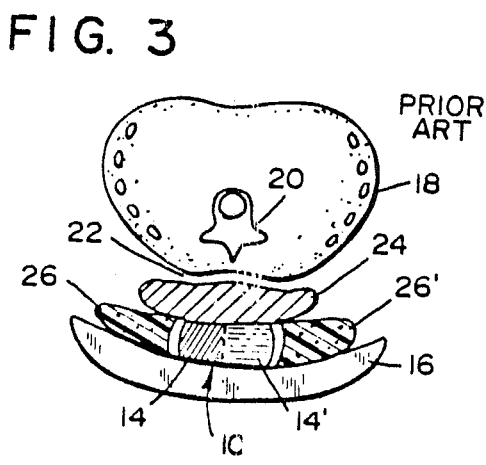
FIG. 3 is a transverse cross section of a patient and a reference phantom according to a further embodiment of the prior art.

Referring now to FIG. 3, a reference phantom 10, containing reference bodies 14 and 14', rests upon table 16. Resilient foam pads 26 and 26', along opposed edges of reference phantom 10, support portions of flexible bolus 24 overhanging reference phantom 10 and aid in supporting patient 18. This prior-art embodiment suffers from the same requirement for coupling using a water-equivalent flexible bolus 24 to fill air gap 22.

Figure 4:
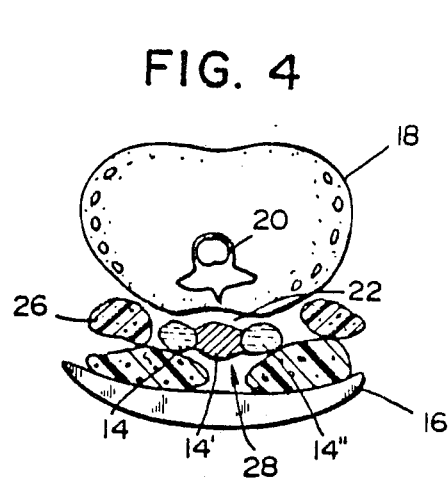
FIG. 4 is a transverse cross section of a patient and a reference phantom according to an embodiment of the invention.

Referring now to FIG. 4, an embodiment of the present invention employs a flexible reference phantom 28 blocked into contact with patient 18 using a plurality of resilient foam pads 26. The resilience of reference phantom 28 permits it to deform into a shape matching the shape of lumbar region 30. The resulting contact substantially eliminates air gap 22 of the prior art (FIG. 3). Thus, direct coupling between flexible phantom 28 and substantially the entire length of lumbar region 30 of patient 18 is achieved without the undesirable effects of water-equivalent bolus material.

Figure 5:
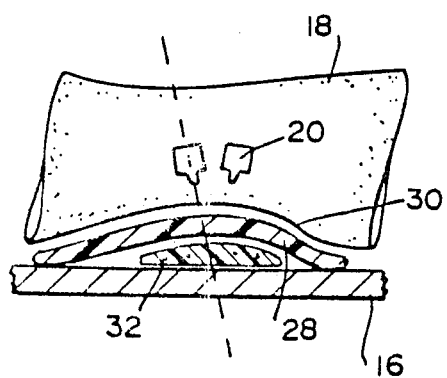
FIG. 5 is a longitudinal cross section of a patient and a reference phantom according to a further embodiment of the invention.

Referring now to FIG. 5, a further embodiment of flexible reference phantom 28 has an unstressed shape forming an arch with a height substantially greater than a height required to attain contact along substantially the entire length of the lumbar region 30 of patient 18. The weight of patient 18 disposed on flexible reference phantom 28 tends to compress and straighten flexible reference phantom 28 until it lies in contact with lumbar region 30 over substantially its entire length. A resilient pad 32 of, for example, an open-cell polyurethane foam, may be employed between table 16 and flexible reference phantom 28 to aid in conforming flexible reference phantom 28 to lumbar region 30. A transverse view of flexible reference phantom 28 (not shown) is similar to reference phantom 10 in FIG. 3.

The resilience and unstressed curved shape of flexible reference phantom 28 permit its use without requiring a flexible bolus 24, and the attendant undesirable effects associated therewith.

Figure 6:
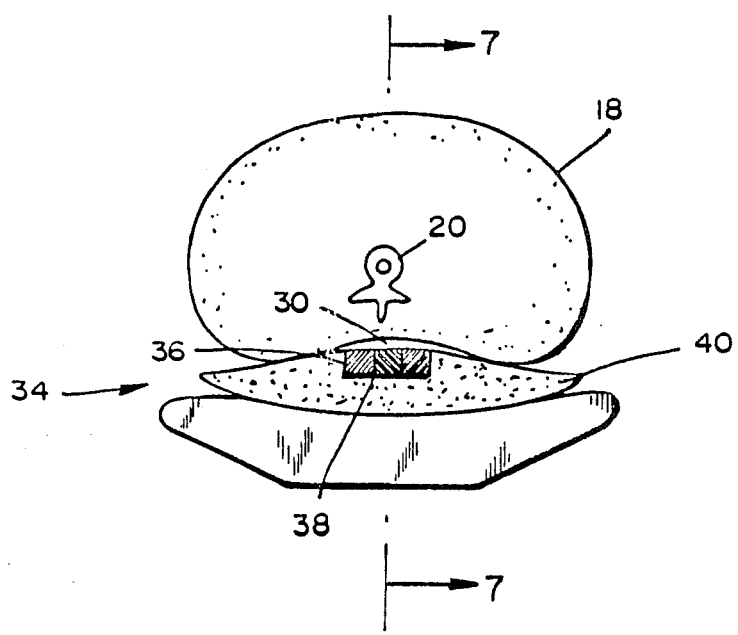
FIG. 6 is a transverse cross section of a patient and a reference phantom according to a further embodiment of the invention.
Figure 7:
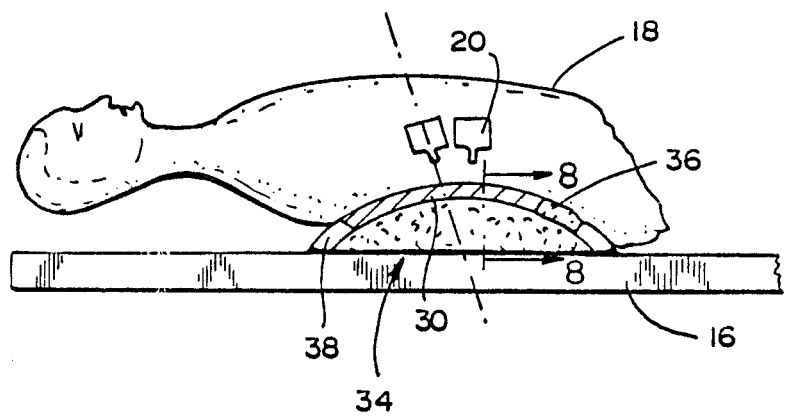
FIG. 7 is a cross section taken along VII—VII in FIG. 6.

Referring now to FIGS. 6 and 7, a flexible reference phantom assembly 34 includes a flexible reference phantom 36 disposed in a slot 38 in a resilient cushion 40. Resilient cushion 40 is supported on table 16.

In its unstressed condition, reference phantom 36 is substantially straight, but has sufficient flexibility to deform into conforming contact with lumbar region 30 of patient 18 under the weight of patient 18 countered by the resisting force of the resilience of resilient cushion 40. The material and stiffness of resilient cushion 40 is matched to the flexibility of reference phantom 36 to achieve the desired result of contact of reference phantom 36 along substantially the entire contiguous length of lumbar region 30. That is, if reference phantom 36 is extremely flexible, the stiffness of resilient cushion 40 may be small while still achieving full contact. On the contrary, if reference phantom 36 is relatively less flexible, an increased stiffness is required in resilient cushion 40 to attain full contact without a substantial air gap between lumbar region 30 and reference phantom 36.

Although any convenient material may be used for resilient cushion 40, one suitable material is an open-celled polyurethane foam material. Besides having a controllable resilience, such material is substantially transparent to X-rays and is thus without the deleterious effects of a water-equivalent bolus.

It is within the contemplation of the present invention that a combination of the pre-curved embodiment of FIG. 5 and the straight embodiment of FIGS. 6 and 7 may be employed. That is, a pre-curved flexible reference phantom 36, having a curvature approximating the curvature of a normal lumbar region 30, may be disposed in slot 38 of FIGS. 6 and 7. In this combination embodiment, only the additional curvature or straightening of flexible reference phantom 36 needed to adapt the curvature of flexible reference phantom 36 to the difference between the normal curvature and that of a particular patient 18 is required.

Figure 8:
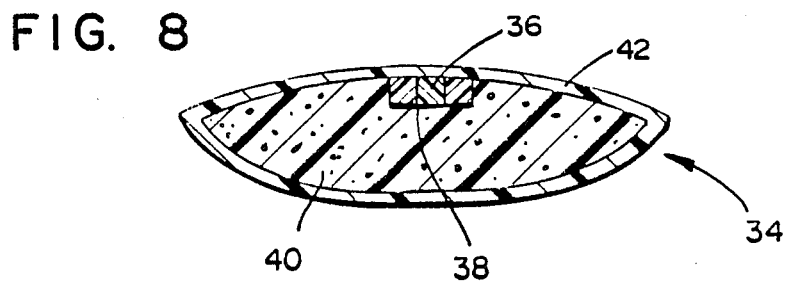
FIG. 8 is an enlarged transverse cross section of the reference phantom system of FIGS. 6 and 7.

Referring now to FIG. 8, flexible reference phantom assembly 34 is preferably enclosed in a cover 42 of any suitable material such as, for example, cloth. In the interest of cleanliness, cover 42 is preferably of a plastic material. Such plastic material should be chosen for its transparency to X-rays and for a composition amenable to cleaning. One suitable material may be, for example, polyvinyl chloride.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A reference phantom for quantitative computer tomography comprising:
   a flexible bar containing a plurality of reference materials;
   said reference materials having predetermined X-ray absorption properties; said bar having a width narrow enough to permit fitting with direct contact between a surface thereof and a substantial portion of a lumbar region of a patient; and
   means for deforming a curvature of said flexible bar into substantially continuous contact over substantially all of said surface with a contiguous portion of said lumbar region, whereby said quantitative computer tomography can be carried out without requiring an absorbing bolus between said reference phantom and said lumbar region.

2. Apparatus according to claim 1 wherein said flexible bar includes an unstressed curvature, and said means for deforming includes at least partly straightening said flexible bar by a weight of said patient thereon.

3. Apparatus according to claim 2 wherein said means for deforming further includes a resilient material between said flexible bar and a surface supporting said weight of said patient.

4. Apparatus according to claim 1 wherein said means for deforming includes:
   a resilient cushion having a dimension substantially co-extensive with said region;
   a slot in an upper surface of said resilient cushion;
   said flexible bar being disposed in said slot;
   a flexibility of said flexible bar and a stiffness of said resilient cushion being effective, in combination, for urging a surface of said reference phantom into contact along substantially all of said contiguous region.

5. Apparatus according to claim 4, further comprising a cover over said flexible bar and said resilient cushion.

6. A reference phantom for quantitative computer tomograph comprising:
   a flexible bar containing a plurality of reference materials;
   said reference materials having predetermined X-ray absorption properties; said bar having a width narrow enough to permit fitting with direct contact between a surface thereof and a substantial portion of a lumbar region of a patient;
   a resilient cushion having a length substantially co-extensive with a contiguous region of said patient and a width exceeding said width of said bar;
   a slot in an upper surface of said resilient cushion;
   said flexible bar being disposed in said slot; and
   a flexibility of said flexible bar and a stiffness of said resilient cushion being effective, in combination, for urging said surface of said reference phantom into contact along substantially all of said lumbar region, whereby said quantitative computer tomography can be carried out without requiring an absorbing bolus between said reference phantom and said lumbar region.

* * * * *

UNITED STATES PATENT AND TRADEMARK OFFICE
CERTIFICATE OF CORRECTION

PATENT NO. : 4,870,666

DATED : Sep. 26, 1989

INVENTOR(S) : Albert H. R. Lonn, et al.

It is certified that error appears in the above-identified patent and that said Letters Patent is hereby corrected as shown below:

Col. 4, line 16, change "equivalent" to --water-equivalent--.

Col. 6, line 9, change "whereby" to --such that--;

line 50, change "reference phantom" to --flexible bar--; and line 52, change "whereby" to --such that--.

Signed and Sealed this

Eighteenth Day of June, 1991

Attest:

HARRY F. MANBECK, JR.

Attesting Officer

Commissioner of Patents and Trademarks